United States Patent [19]

Nielsen

[11] 4,080,968

[45] Mar. 28, 1978

[54] OBSTETRICAL SUPPORT AND PAN ARTICLE

[76] Inventor: Irene L. Nielsen, 2363 McMillan St., Eugene, Oreg. 97405

[21] Appl. No.: 730,190

[22] Filed: Oct. 6, 1976

[51] Int. Cl.² ............................................. A61B 17/42
[52] U.S. Cl. ........................................ 128/292; 4/112; 128/361
[58] Field of Search ................. 128/31, 292, 275, 361; 4/110, 112; 269/322, 327, 328

[56] References Cited

U.S. PATENT DOCUMENTS

| | | | |
|---|---|---|---|
| 1,045,793 | 11/1912 | Houdard | 4/112 |
| 2,198,804 | 4/1940 | Carlsson | 128/292 |
| 2,359,830 | 10/1944 | Deckert | 4/112 X |
| 3,532,336 | 10/1970 | Baker | 128/292 X |

FOREIGN PATENT DOCUMENTS 720,128  12/1939  Germany .......................... 128/361

Primary Examiner—Dalton L. Truluck
Attorney, Agent, or Firm—James D. Givnan, Jr.

[57] ABSTRACT

An article for placement on a bed or other supporting surface and on which a pregnant woman's buttocks and lower back are supported during childbirth. A portion of the article defines a receptacle for the reception of fluids incident to childbirth. The receptacle is recessed to also provide a work area for the person performing the delivery. A raised portion of the article is concave along its upper surface to confine the buttocks against slippage. A relieved portion of the receptacle wall receives the head and neck of the child during removal of fluid from the respiratory system. Handgrips facilitate muscular contractions of the woman. An irregular surface on the underside of the article prevents slippage on a supporting surface.

3 Claims, 2 Drawing Figures

OBSTETRICAL SUPPORT AND PAN ARTICLE

BACKGROUND OF THE INVENTION

The present invention relates generally to an article for supporting a woman in an elevated position.

In the prior art are a number of devices intended for positioning the woman in a preferred position. For the most part such equipment is intended for use within a fully equipped hospital delivery room and requires other costly, related equipment for its use. With an increasing number of deliveries now being performed in clinics a need exists for an uncomplicated article which both positions the woman during childbirth while coinjointly providing a work area for the person performing the delivery.

SUMMARY OF THE PRESENT INVENTION

The present invention is embodied within a structure for placement on a bed or similar surface which positions the woman in an inclined manner while providing a receptable for fluids lost during childbirth.

The present device is of monolithic construction having, adjacent one end, a curved surface in elevated relationship to the bed, delivery table, etc., which surface retentively supports the woman's raised buttocks. A rearwardly extending, upwardly curved portion of the curved surface provides support for the woman's lower back as well as positions the woman in a semi-reclined position. Integral with the above described support is a pan-like structure having an outer wall and a bottim wall jointly defining a work area which provides space for unrestricted manipulation of the baby during childbirth. A recessed area within the outer wall receives the baby's head during aspiration. Handgrips on the sides of the device permit the woman to exert desired muscular effort during childbirth. An irregular bottom surface of the device prevents undesired slippage of the device relative to a supporting surface whether it be a bed, surgical table, etc. In one form a regular bottom may be provided by transversely extending ridges to prevent slippage of the article.

Important objectives of the present obstetrical device include the provision of a portable, monolithic structure for use in positioning a woman during childbirth while providing a highly accessible work area for the doctor or mid-wife and additionally a receptable for body fluids; the provision of an obstetrical device having a recessed wall structure for the reception of the baby's neck and head during aspiration whereby the neck and head of the child are located so as to facilitate etry of aspiration devices; the provision of an obstetrical device having handgrips to enhance the woman's capability of assisting childbirth by applying muscular forces, the provision of an obstetrical device having an irregular underside to prevent undesired movement of the device on supporting surface; the provision of an obstetrical article shaped at one of its ends so as to permit a person assisting childbirth to be positioned behind the woman to support her in a semi-reclined position.

DETAILED DESCRIPTION OF THE PREFERRED EMBODIMENT

Figure 1:
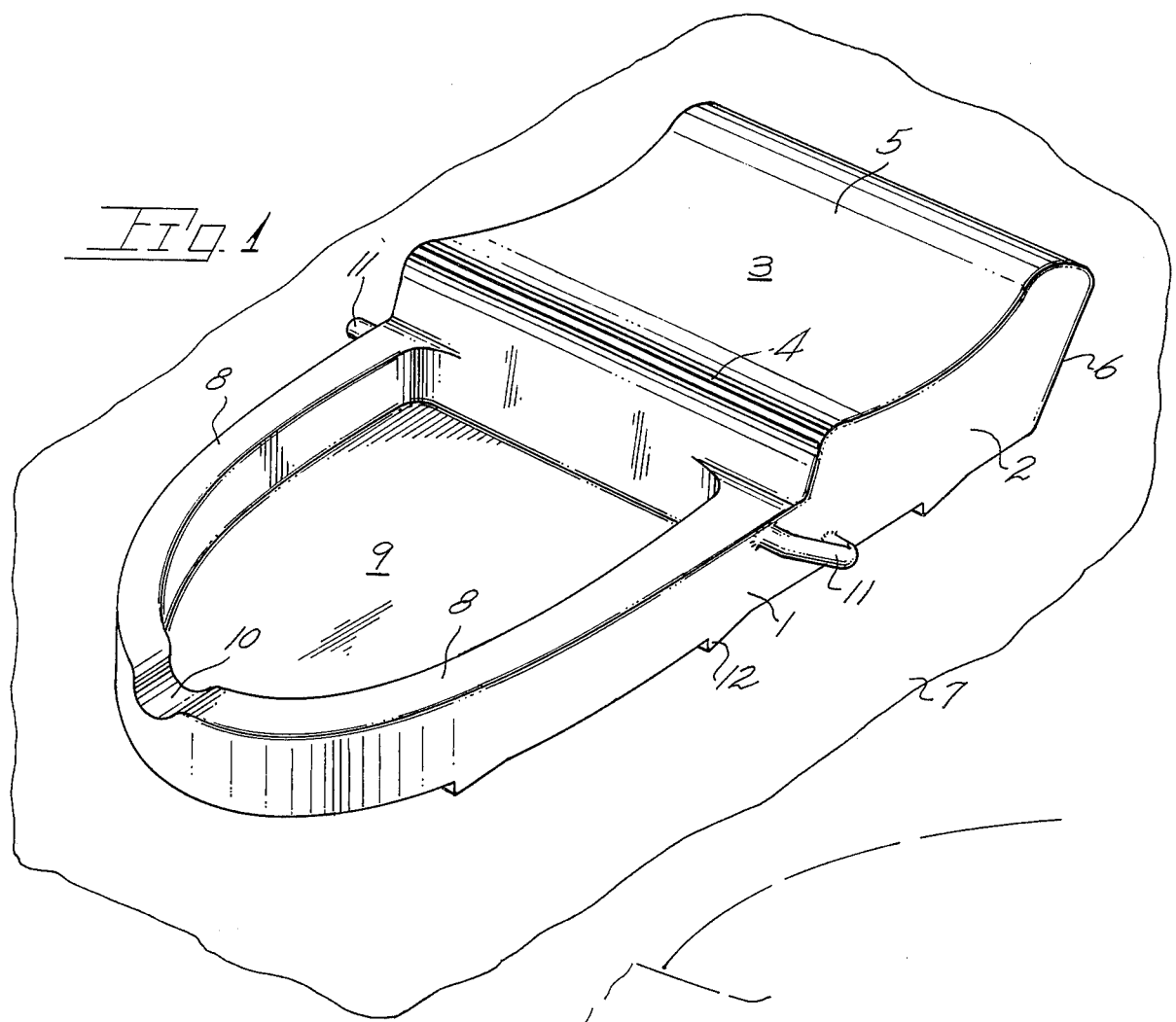
FIG. 1 is a perspective view of the present obstetrical article in place on a supporting surface.

With continuing attention to the accompanying drawing, wherein applied reference numerals indicate parts similarly identified in the following description, the reference number 1 indicates the main body of the obstetrical article with an enlarged or elevated portion indicated at 2.

Figure 2:
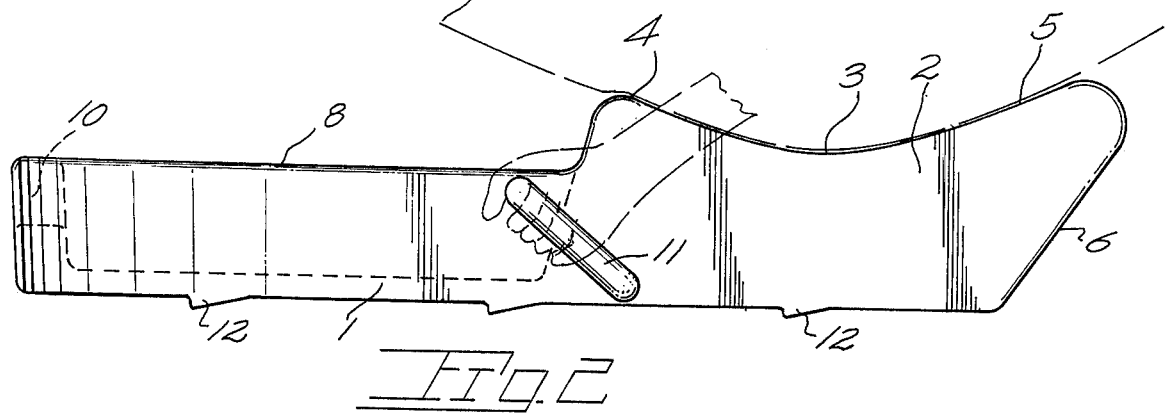
FIG. 2 is a side elevational view of the article with a body portion shown in phantom lines.

A concave upper surface area at 3 is curved from front to rear to receive the buttocks of the woman per FIG. 2. A barrier at 4 is embodied within a raised portion which serves to confine the buttocks against forward displacement. A curved segment 5 of surface 3 is configured so as to comfortably support the lower back at an upwardly inclined angle. The rearward end of the device is embodied in a rearwardly inclined wall 6 which extends downwardly to a supporting surface such as a bed. Wall 6 is canted for the purpose for permitting the woman's lower back to be fully supported by an adjacent article not shown.

A pan-like structure is defined by a curved outer wall 8 in conjunction with a bottom 9. Wall 8 has a recessed area 10 therein which is of a size and elevation to support the head and neck of a new born baby so as to best position same for aspiration efforts. In such instances it is highly advantageous, of course, to have the baby's head tilted back.

Indicated at 11 are a pair of handgrips which the woman may grasp during childbirth to permit her to exert muscular effort facilitating the birth process. The handgrips are preferably inclined so as to permit convenient grasping.

An irregular bottom surface is provided on the article to assure article retention on a supporting surface. Such undesired shifting is prevented by a series of projections 12 which embed themselves under the weight of the woman into surface 7.

In use, the woman's buttocks are placed on curved surface 3. The height of surface 3 locates the buttocks a sufficient distance above bed surface 7 to provide an adequate work area above bottom wall 9 of the article. Delivery of the baby takes place above bottom wall 9 which is substantially coplanar with bed surface 7.

The device is of a size to permit it to be easily carried from one using site to another and to autoclave.

While I have shown but one embodiment of the invention it will be apparent to those skilled in the art that the invention may be embodied still otherwise without departing from the spirit and scope of the claimed invention.

Having thus described the invention what is desired to be secured under a Letters Patent is:

1. An obstetrical article for use during childbirth and supporting a woman's buttocks in upwardly space relationship to a bed or like surface, said article comprising,
   a support having a concave surface on which the woman's buttocks are rested to upwardly space same above the bed surface,
   a pan-like structure merging at one end with said support and defined by an upstanding perimetrical wall in a horizontal plane below said concave surface and a bottom wall with the bottom wall defining the lower limit of a work area, said upstanding wall defining a downwardly extending recessed area formed therein and within which the baby's neck and head may be supported during aspiration efforts, and said support having a raised portion which confines the buttocks, said supporting surface additionally including an upwardly curved rear wall for support of the woman's lower back.

2. The obstetrical article claimed in claim 1 additionally including a bottom surface having a series of transversely extending parallel ridges to prevent slippage of the articles on a supporting surface.

3. The obstetrical article claimed in claim 1 additionally including inclined handgrips extending from the sides of the article for grasping by the woman during childbirth.

* * * * *